(12) United States Patent
Hecke et al.

(10) Patent No.: US 9,603,606 B2
(45) Date of Patent: Mar. 28, 2017

(54) DENTAL INSTRUMENT

(71) Applicant: Gebr. Brasseler GmbH & Co. KG, Lemgo (DE)

(72) Inventors: Josef Hecke, Doerentrup (DE); Friedrich Wilhelm Meier, Blomberg (DE); Markus Niemeier, Lage (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 126 days.

(21) Appl. No.: 14/607,299

(22) Filed: Jan. 28, 2015

(65) Prior Publication Data

US 2015/0216537 A1 Aug. 6, 2015

(30) Foreign Application Priority Data

Feb. 3, 2014 (DE) .................. 10 2014 201 899

(51) Int. Cl.
*A61B 17/16* (2006.01)
*A61C 3/02* (2006.01)
(52) U.S. Cl.
CPC .............. *A61B 17/16* (2013.01); *A61C 3/02* (2013.01); *A61B 2017/1602* (2013.01)
(58) Field of Classification Search
CPC .... A61B 17/16; A61B 2017/1602; A61C 3/02
See application file for complete search history.

(56) References Cited

U.S. PATENT DOCUMENTS

| 6,299,445 | B1 | 10/2001 | Garman |
| 2003/0068597 | A1 | 4/2003 | Garman |

FOREIGN PATENT DOCUMENTS

| CH | 651746 | 10/1985 |
| DE | 19734016 | 2/1999 |
| DE | 19810284 | 9/1999 |
| DE | 69636020 | 8/2006 |
| DE | 202008018364 | 4/2013 |
| EP | 1184004 | 3/2002 |
| WO | 2004/021913 | 3/2004 |

OTHER PUBLICATIONS

English translation and Office Action dated Aug. 12, 2014 issued by the German Patent Office for counterpart German application No. 10 2014 201 899.4.
English translation and European Search Report dated Apr. 28, 2015 for counterpart European application No. 15152844.5.

*Primary Examiner* — Rex R Holmes
(74) *Attorney, Agent, or Firm* — Shuttleworth & Ingersoll, PLC; Timothy J. Klima

(57) ABSTRACT

The present invention refers to an instrument, configured as a dental instrument or surgical instrument, the instrument comprising a shaft and a substantially rotation-symmetrical head which is attached to the shaft and provided with a plurality of cutting blades, the cutting blades being arranged distributed around the whole circumference of the head, in relation to a centric rotational axis of the instrument, characterized in that each cutting blade has a geometry differing from the other cutting blades.

9 Claims, 3 Drawing Sheets

DENTAL INSTRUMENT

This application claims priority to German Patent Application DE102014201899.4 filed Feb. 3, 2014, the entirety of which is incorporated by reference herein.

The present invention refers to an instrument, particularly a dental instrument or a surgical instrument, according to features described herein.

In detail, the present invention refers to an instrument comprising a shaft and a substantially rotation-symmetrical head which is attached to the shaft and which is provided with a plurality of cutting blades. The instrument is rotatable about a centric rotational axis. The cutting blades are arranged around the whole circumference of the head, in relation to the rotational axis, distributed on the head.

The prior art discloses very different designs of such instruments. Reference is made by way of example to DE 198 10 284 A1 or DE 197 34 016 A1.

On the whole, the design of such instruments is always based on the concept that these must exhibit an adequate removal rate or cutting performance and a satisfactory service life. Furthermore, the demand is made that such instruments should show a low-vibration operation.

The known instruments, which are also called milling cutters, normally comprise circumferentially distributed identical cutting blades with identical cutting blade geometries and pitches. In addition to a first toothing formed by first cutting blades, a second toothing or secondary toothing may also be formed, which is also of the cutting type and the cutting blades of which exhibit for instance a twist opposite to the main cutting blades.

Furthermore, it is known that the basic toothing of such an instrument is configured such that this toothing is circumferentially divided into plural groups. In the individual groups different toothings may be provided these, however, are the same within the group. Upon rotation of the instrument this yields a sequence of the engaged cutting blades from a first group to a second group. Even such designs do not always meet the expectations regarding the removal rate and the low-vibration true running.

It is the object of the present invention to provide an instrument of the afore-mentioned type which is distinguished by a high removal rate and a long service life and by low-vibration running.

The object is achieved through features described herein. The present description describes show further advantageous designs.

According to the invention it is thus intended that the cutting blades which are distributed around the circumference of the head are configured such that each cutting blade in relation to the other cutting blades shows a different geometry. Hence, on its head the instrument does not have a cutting blade that is identical with another cutting blade. Rather, all cutting blades have a different configuration.

According to the invention the different design of the cutting blades may regard the pitch (angular pitch in circumferential direction), the wedge angle, the clearance angle, the rake angle and/or the cutting blade depth. All further differences of the cutting blades are herewith encompassed according to the invention.

The instrument according to the invention is preferably configured such that all of the cutting blades are arranged on a common rotary circle which has its center in the rotational axis of the instrument. This guarantees a low-vibration and uniform true running of the instrument.

The instrument according to the invention may be made from a metallic material, a ceramic material or a plastic material. The cutting blades can be produced by machining, e.g. milling or grinding. The cutting blades can particularly be produced by means of a CNC machine.

Upon rotation of the instrument and due to the different geometry of the cutting blades there is a cutting geometry that is always changed with respect to the preceding cutting blade. As has been mentioned, this particularly regards the cutting blade angles (wedge angle, rake angle, clearance angle). However, on account of the different configuration of the individual cutting blades, the cutting blade depth is also changing, so that a different cutting space is also formed. This leads to improved removal rates. The resulting different loads on the individual cutting blades lead to a long service life of the instrument.

According to the invention it is possible to mount cutting blades as a main toothing on the head according to the above-described solution of the invention and to form cutting blades of a secondary toothing in addition. This toothing may e.g. have a pitch or a twist differing from that of the cutting blades of the main toothing. It is particularly advantageous when the cutting blades of the secondary toothing also differ from one another in their design. However, they may also be of the same design.

Preferably, the cutting blades according to the invention extend substantially over the total axial length of the head. According to the invention the head of the instrument may have standard shapes, for instance, cylindrical, conical shapes or crowned or rounded forms, e.g. the form of a pear, a flame or a bud. In this respect all of the head shapes known from the prior art can be provided with the toothing according to the invention.

The instrument according to the invention may be configured such that the cutting blades of the main toothing extend in a straight line or in twisted form along the head. The cutting blades can be configured such that they are made to extend on the front side relative to the center of the instrument (relative to the rotational axis). It is however also possible to configure the cutting blades such that they converge on the front side to form at least one cross cutting blade. The subdivision of the groups in circumferential direction into individual sections or groups is also possible. These groups may e.g. differ with respect to the pitch or the twist. The configuration of the cutting blades in groups may also serve the said design of at least one cross cutting blade on the front end portion of the instrument. It is also possible to arrange the cutting blades in two or four groups which are mirrored or made symmetrical with respect to a central plane comprising the rotational axis. Different cutting blades or teeth are then formed in each group.

In all of the above-described configuration variants it is intended according to the invention that all cutting blades are made different from one another. Hence, all cutting blades differ from one another on the head; there are no two identical or like cutting blades.

In a further, particularly advantageous configuration of the invention, it is intended that the cutting blade geometries are defined at random, possibly with the help of a random generator. Hence, the cutting blades are configured at random with respect to their design (pitch, wedge angle, clearance angle, rake angle and/or cutting blade depth) or with respect to further parameters. This means that no instrument resembles the other, but that all instruments adhere to the same basic concept.

The invention will now be described with reference to are embodiment taken in conjunction with the drawing, in which.

Figure 1:
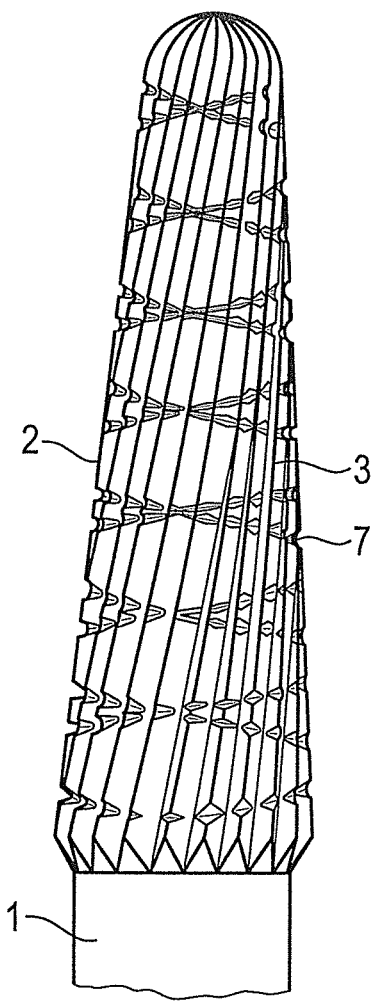
FIG. 1 is a side view of a head of an instrument according to the invention.

FIG. 1 shows an embodiment of an instrument according to the invention (dental instrument or surgical instrument) in partial side view, a head 2 being shown which is conically shaped, rounded on its front side and attached to a shaft 1. The head 2 is provided with twisted cutting blades 3 which are configured according to the invention, and comprises secondary cutting blades 7 in addition.

Figure 2:
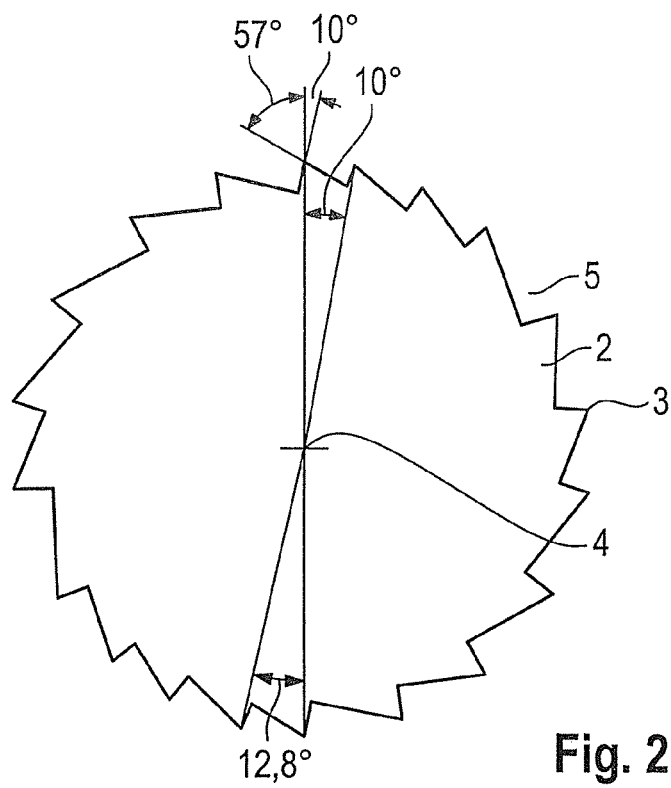
FIG. 2 is a sectional view of an embodiment of the instrument according to the invention.
Figure 3:
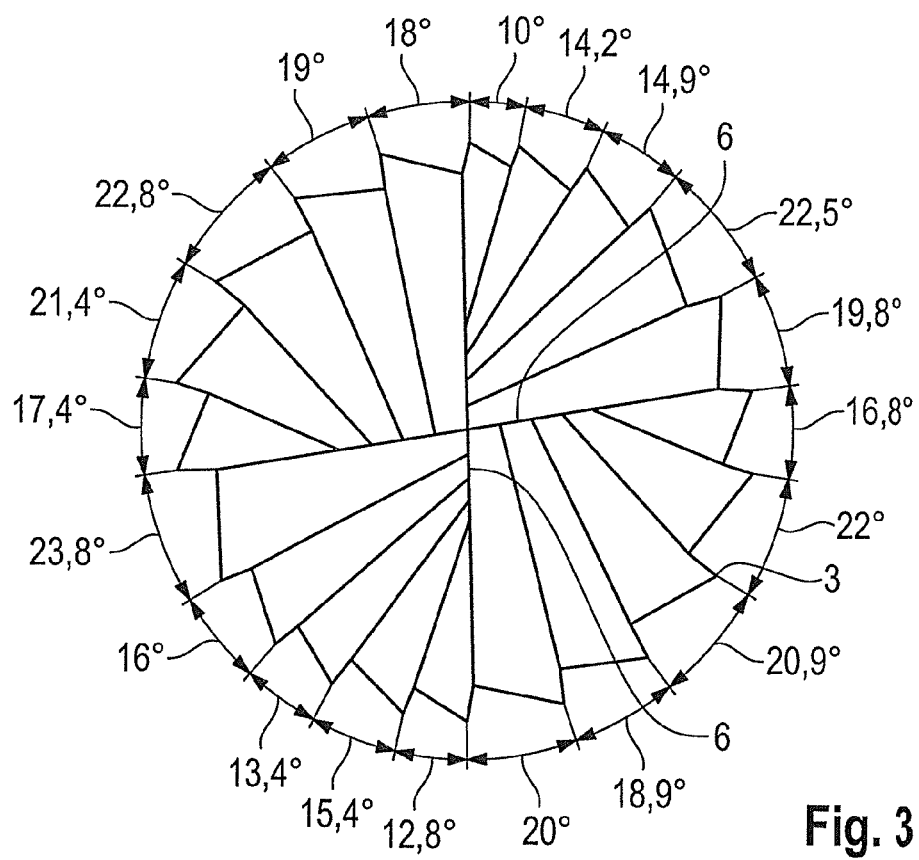
FIG. 3 is a front top view on the instrument shown in FIG. 2.

FIGS. 2 and 3 show a detail view of an embodiment of the to thing according to the invention. FIG. 2 is a sectional view in a radial plane perpendicular to a rotational axis 4. As can be seen, the instrument comprises a plurality of cutting blades 3 distributed around the circumference. As shown in FIG. 1, the cutting blades 3 may be configured to be coiled or twisted. However, it is also possible to make them straight. The tips of all cutting blades are positioned on a rotary circle 5, resulting in an envelope which is rotation-symmetrical with respect to the rotational axis 4 when the instrument is put into rotation around the rotational axis 4.

In the upper picture half of FIG. 2, it is illustrated how the cutting blade is configured. It has a rake angle of 10° and is provided with a pitch of 10° relative to the next neighboring cutting blade. The illustration of FIG. 2 further shows the associated wedge angle of the cutting blade. This follows from the tooth angle of 57° plus the negative rake angle of 10°.

In the lower picture half, FIG. 2 shows a cutting blade opposite to the above-described cutting blade; this opposite cutting blade is provided with a pitch of 12.8° with respect to the next cutting blade and thus differs from the cutting blade positioned at the top in FIG. 2.

FIG. 3 shows a frontal view of the instrument shown in FIG. 2. Here, the number of cutting blades or teeth is 20; these respectively differ in the pitch (circumferential angle). FIG. 3 shows different angles by way of example. It becomes apparent that no cutting blade resembles the other. Owing to the different pitches one obtains different cutting blade geometries and different cutting blade depths, as has been explained above.

Figure 4:
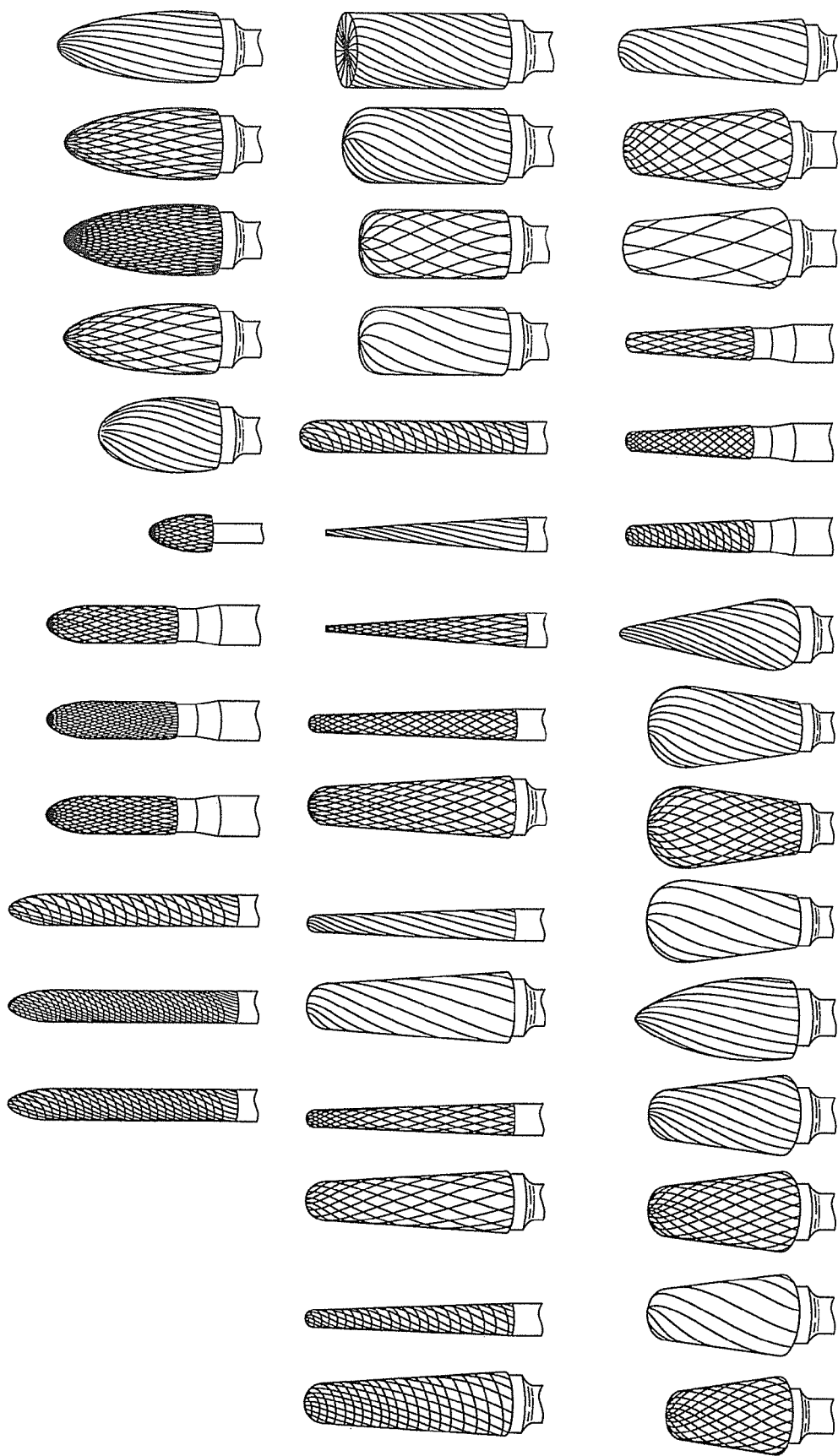
FIG. 4 is an illustration of different head shapes of the instrument according to the invention.

In a schematic side view, FIG. 4 shows a plurality of possible designs of a head of an instrument according to the invention. These heads may have any desired head shapes, e.g. cylindrical or conical, each with a rounding or flattening at the front side, and other shapes, such as pear shape, flame shape, bud shape, or the like.

LIST OF REFERENCE NUMERALS 1 shaft
2 head
3 cutting blade
4 rotational axis
5 rotary circle
6 cross cutting blade
7 secondary cutting blade

The invention claimed is:

1. A dental instrument, comprising:
a shaft,
a substantially rotation-symmetrical milling cutter head having a solid base circle which is attached to the shaft and a plurality of cutting blades attached to the solid base circle, the cutting blades distributed around an entire circumference of the head, in relation to a centric rotational axis of the instrument,
wherein each cutting blade has a geometry in a radial plane perpendicular to the rotation axis differing from the other cutting blades,
wherein each cutting blade has at least one chosen from a different pitch, a different cutting depth, a different wedge angle, a different rake angle and a different clearance angle than the other cutting blades.

2. The dental instrument according to claim 1, wherein all of the cutting blades are arranged on a common rotary circle having a center on the rotational axis.

3. The dental instrument according to claim 1, wherein the cutting blades are formed substantially over an entire axial length of the head.

4. The dental instrument according to claim 1, wherein the cutting blades are arranged in two or more groups.

5. The dental instrument according to claim 1, wherein a plurality of secondary cutting blades of at least one secondary toothing are formed on the head, wherein each secondary cutting blade has a geometry in a radial plane perpendicular to the rotation axis differing from the other secondary cutting blades.

6. The dental instrument according to claim 1, wherein the cutting edges are configured to extend on a front side of the head relative to the rotational axis.

7. The dental instrument according to claim 1, wherein the cutting blades are arranged on a front side of the head to form at least one cross cutting blade.

8. The dental instrument according to claim 1, wherein the cutting blades are straight.

9. The dental instrument according to claim 1, wherein the cutting blades are twisted.

* * * * *